US00PP22815P2

(12) United States Plant Patent
Warren

(10) Patent No.: US PP22,815 P2
(45) Date of Patent: Jun. 26, 2012

(54) BUR OAK TREE NAMED 'JFS-KW3'

(50) Latin Name: *Quercus macrocarpa*
Varietal Denomination: JFS-KW3

(75) Inventor: Keith S. Warren, Gresham, OR (US)

(73) Assignee: J. Frank Schmidt & Son Co., Boring, OR (US)

( * ) Notice: Subject to any disclaimer, the term of this patent is extended or adjusted under 35 U.S.C. 154(b) by 195 days.

(21) Appl. No.: 12/657,697

(22) Filed: Jan. 25, 2010

(51) Int. Cl.
*A01H 5/00* (2006.01)

(52) U.S. Cl. ..... Plt./225

(58) Field of Classification Search ..... Plt./225
See application file for complete search history.

(56) References Cited

U.S. PATENT DOCUMENTS

PP11,431 P * 6/2000 Cully ..... Plt./225
PP21,359 P2 * 10/2010 Cully ..... Plt./225

OTHER PUBLICATIONS

Anonymous. "Urban Pinnacle Oak". Available at: http://www.jfschmidt.com/pdfs/urbanpinnacleoak.pdf accessed Sep. 28, 2011.*
Anonymous. "JFS Introductions *Quercus macrocarpa* 'JFRS-KW3' P.A.F" Available at: http://www.jfschmidt.com/introductions/urbanpinnacle/index.html accessed Sep. 28, 2011.*

* cited by examiner

*Primary Examiner* — Wendy C Haas
(74) *Attorney, Agent, or Firm* — Klarquist Sparkman, LLP

(57) ABSTRACT

A variety of bur oak which combines a straight, upright trunk, a narrowly oval to narrowly pyramidal upright growth habit, glossy dark green foliage, and resistance to powdery mildew and anthracnose.

9 Drawing Sheets

Latin name of the genus and species: *Quercus macrocarpa*.
Variety denomination: 'JFS-KW3'.

BACKGROUND

During the summer and fall of 1998, I began a search for improved varieties of bur oak, *Quercus macrocarpa*. I examined a few thousand two year old nursery grown trees of *Quercus macrocarpa* growing in rows at a nursery in Boring, Oreg. These trees had been planted from seed. At various times during the summer and fall, I tagged the most promising looking trees in these nursery rows. I was selecting for disease resistance, straightness, growth rate, foliage appearance, fall color, and defoliation. By the time the trees had gone dormant, I had selected what I believed to be the 21 most promising individual trees in the block.

In the spring of 1999, I transplanted these trees into testing rows in the nursery. I labeled each tree, and over the next two summers I evaluated the appearance and performance of these trees and recorded notes. After two years of evaluation, I selected the best seven trees and transplanted them in 2001 into a long term evaluation block with wider spacing. I rejected and destroyed the remaining 14 trees as being of lesser quality.

Over the next several years, I examined my seven selected bur oak trees, photographed them, and took detailed notes regarding their features. In this evaluation, my new variety 'JFS-KW3' emerged as the best selection in terms of the superior characteristics that I was seeking. The parent trees to 'JFS-KW3' were unnamed, unpatented trees of the species *Quercus macrocarpa*. In 2003, 2005, 2006, 2007, and 2008, I propagated small plots test plots of my new variety at the nursery in Boring, Oreg., by chip budding onto seedling *Quercus macrocarpa* rootstock. From this propagation, I established that the characteristics of a straight upright trunk, a narrowly oval to narrowly pyramidal upright growth habit, dark green foliage and resistance to powdery mildew (*Erysiphe alphitoides*) and anthracnose (*Apiognomonia quercina*) of my new variety are unique and firmly fixed in each successive generation.

In the fall of 2006, the original tree of my new variety began producing acorns. These acorns were unusual in that they were extremely small acorns for the species, a desirable characteristic for landscape use. The acorns have yet to be observed in the asexually propagated progeny because the progeny are too young to have acorns, but the acorn characteristic is expected in this progeny.

SUMMARY

This new cultivar possesses a unique combination of characteristics in that it combines a straight upright trunk, a narrowly oval to narrowly pyramidal upright growth habit, glossy dark green foliage, and resistance to powdery mildew and anthracnose.

BRIEF DESCRIPTION OF THE DRAWINGS

The colors of an illustration of this type may vary with lighting conditions and, therefore, color characteristics of this new variety should be determined with reference to the observations described herein, rather than from these illustrations alone.

DETAILED BOTANICAL DESCRIPTION

Figure 1:
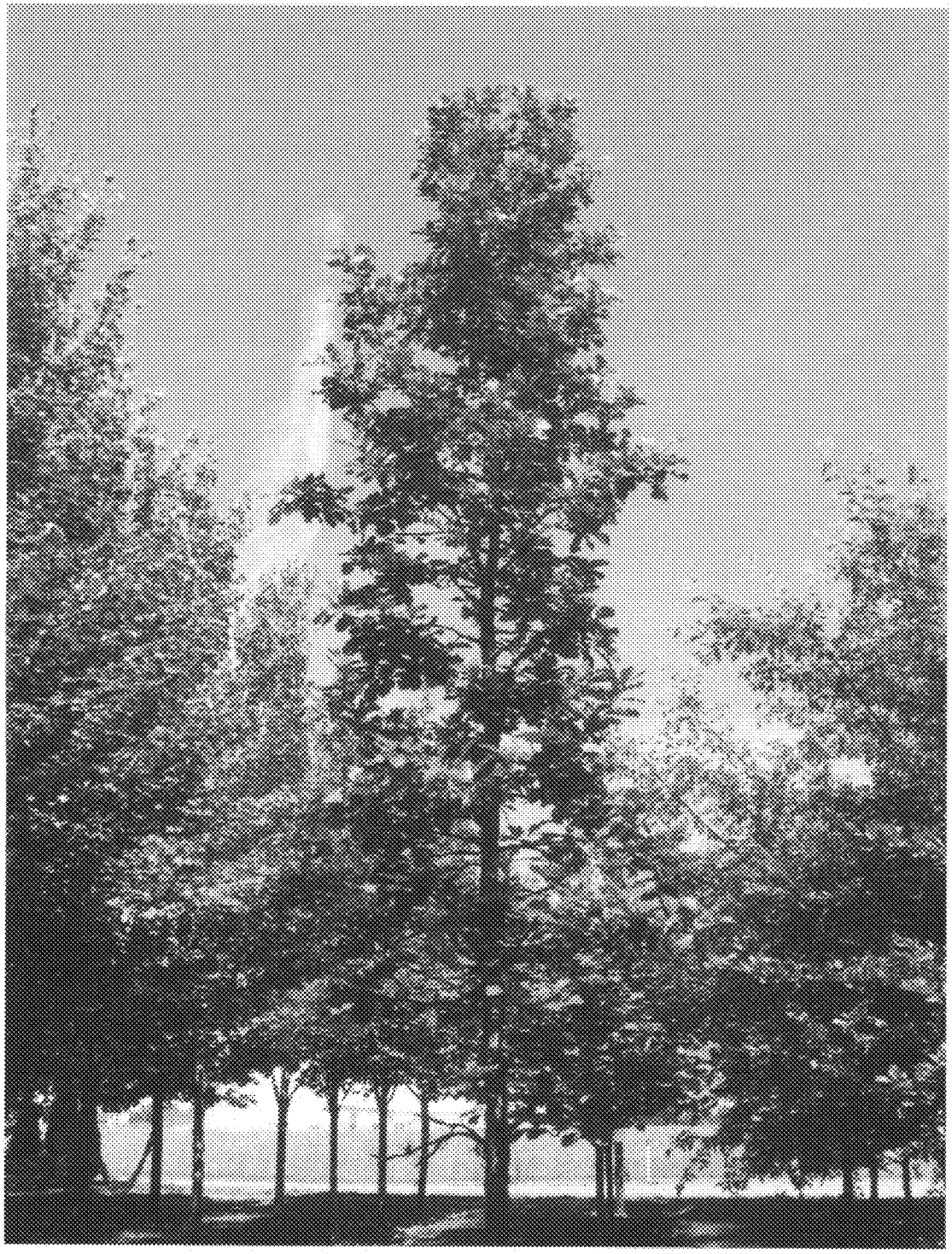
FIG. 1: Shows the original tree, illustrating the upright growth habit, straight trunk, and the narrow pyramidal to narrow oval form.
Figure 2:
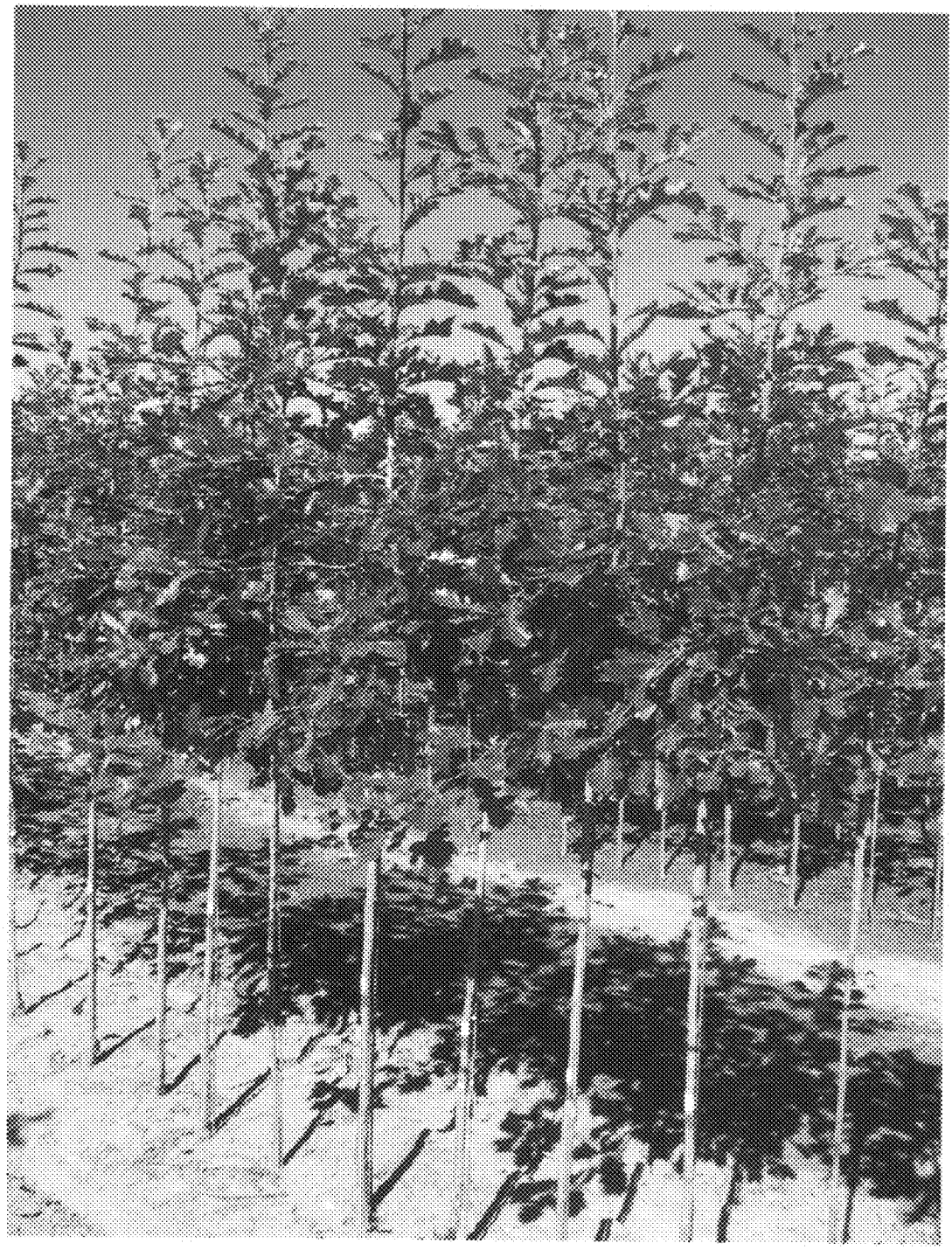
FIG. 2: Shows two year old nursery grown trees, illustrating the straight trunk and central leader, the upright habit, and the short side branches.
Figure 3:
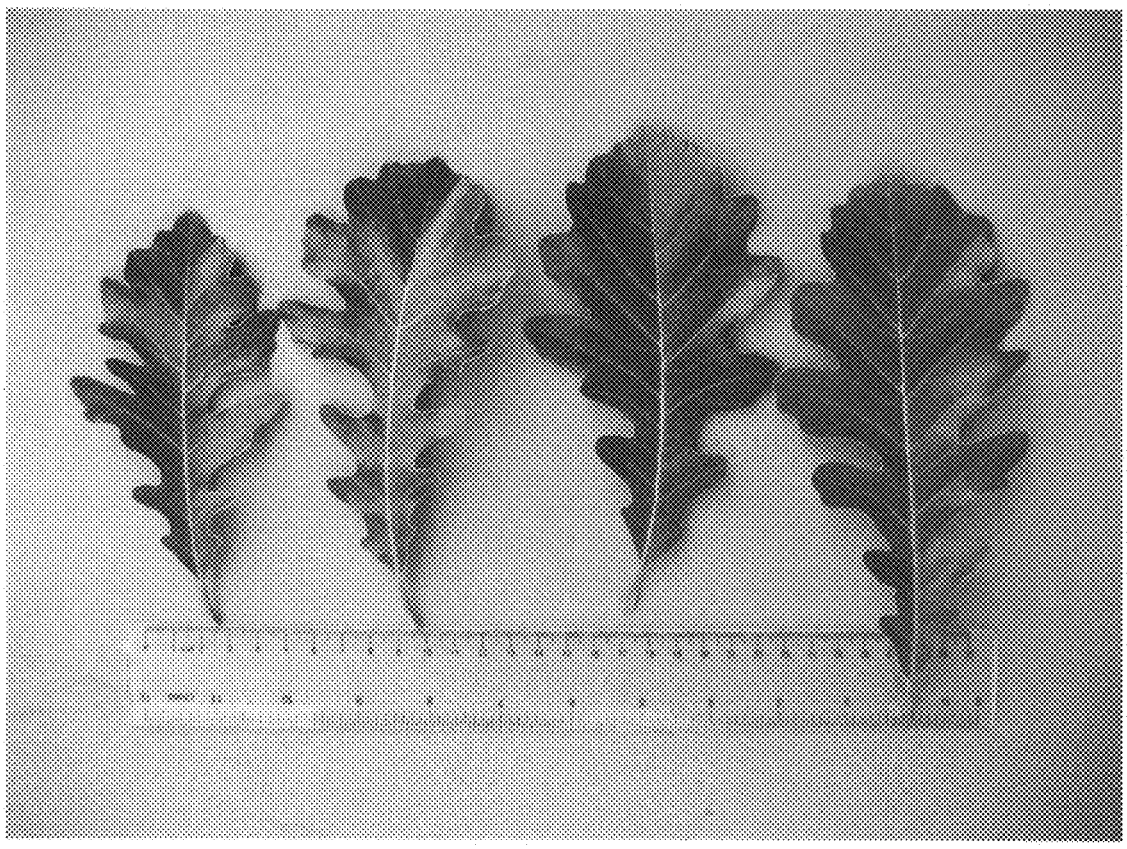
FIG. 3: Shows the upper surface of typical summer leaves with dark green color and a glossy surface.
Figure 4:
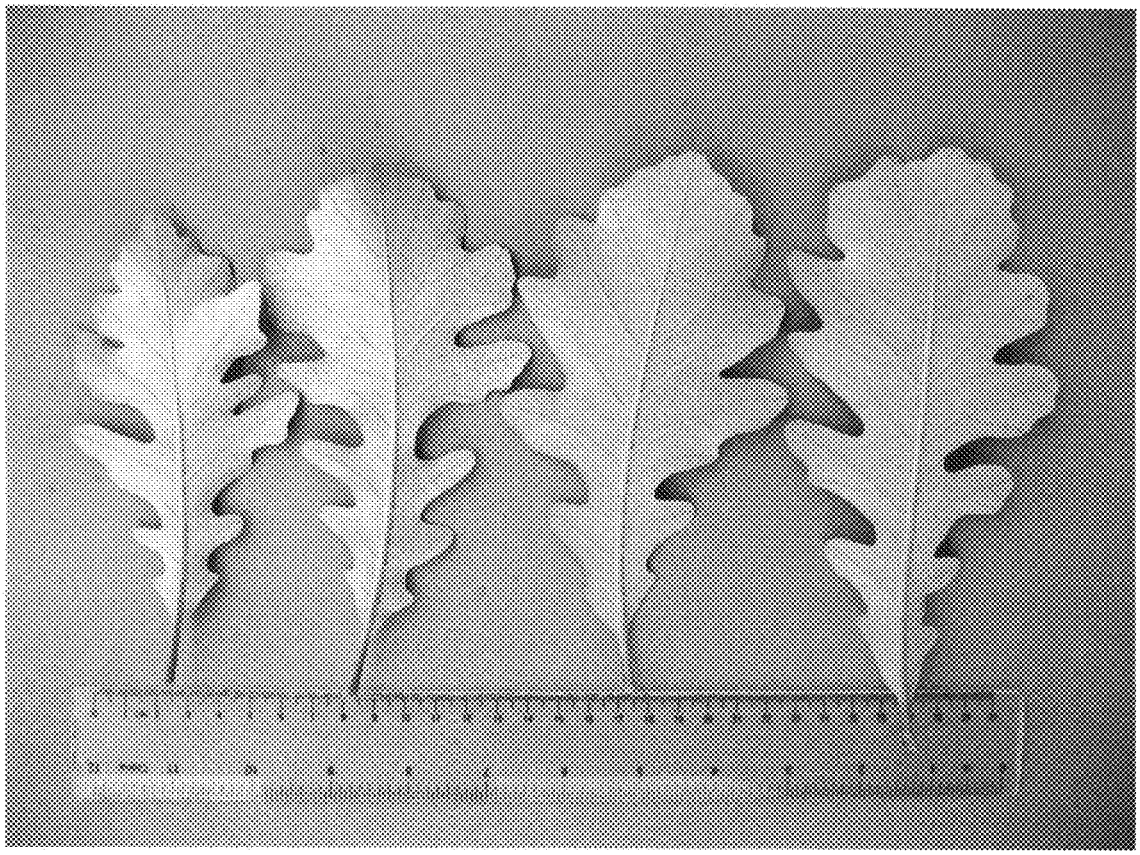
FIG. 4: Shows the lower surface of typical summer leaves.
Figure 5:
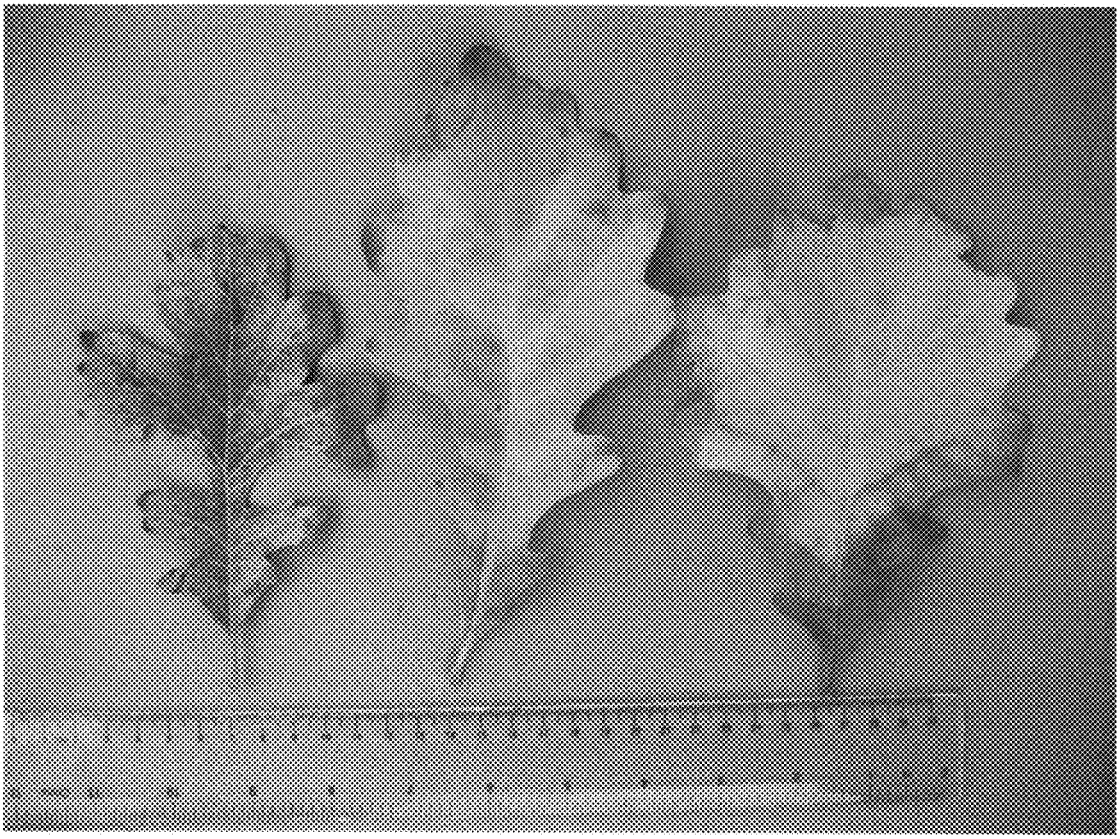
FIG. 5: Shows the top surface of typical leaves displaying fall color.
Figure 6:
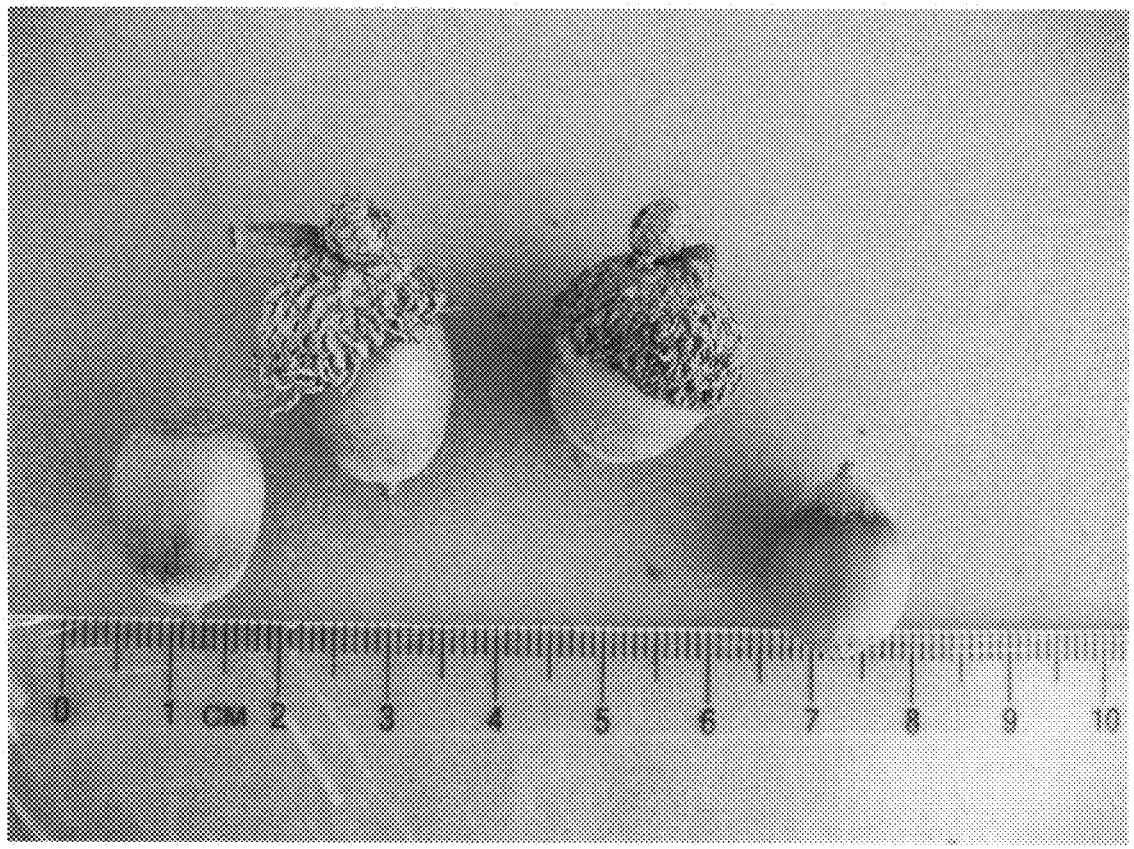
FIG. 6: Shows typical acorns and nuts from the original tree of my variety. The two upper fruits in this figure are complete acorns, with caps and each with a second small undeveloped aborted acorn attached to the top of the cap. On the complete acorn at center-right, the cap's marginal fringe has been worn away by abrasion in the tree canopy. The lowermost (outer) two fruits are typical nuts which have been removed from their caps.
Figure 7:
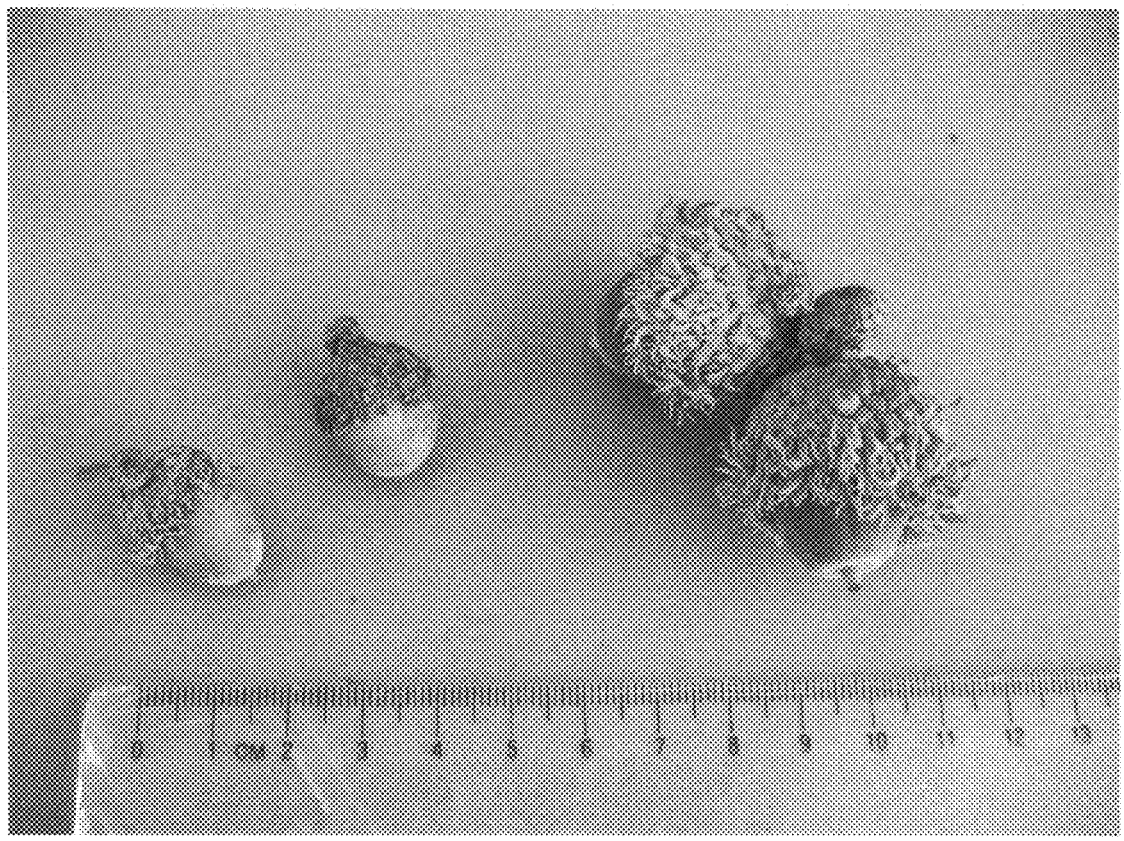
FIG. 7: Shows two typical acorns of 'JFS-KW3' from the original tree of my variety on the left in comparison to two typical and much larger acorns of the species *Quercus macrocarpa* on the right. This figure illustrates the relatively smaller acorn size of the acorns from the original tree of my new variety.
Figure 8:
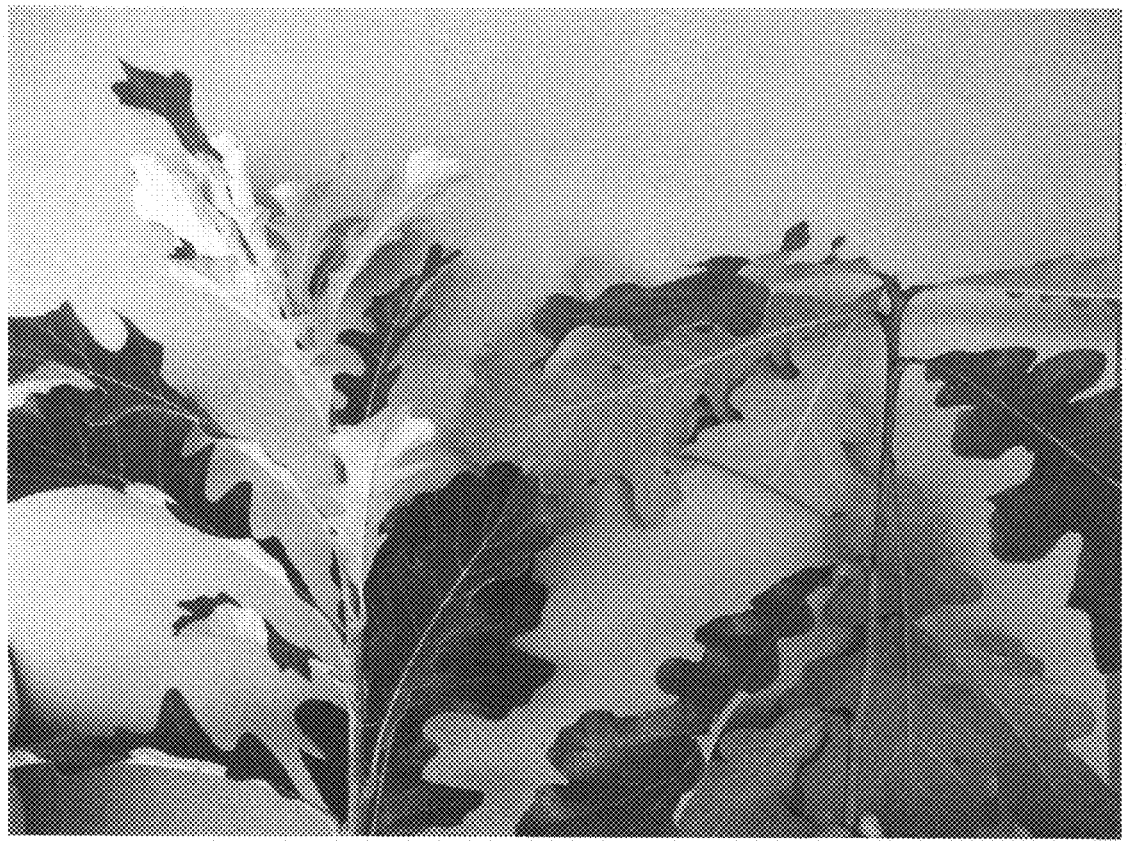
FIG. 8: Shows a new growth branch tip of 'JFS-KW3' on the left and a new growth branch tip of a typical *Quercus macrocarpa* seedling tree on the right, and illustrates the upward orientation of the leaves and petioles of my new variety compared to the much more horizontal orientation of the seedling tree.
Figure 9:
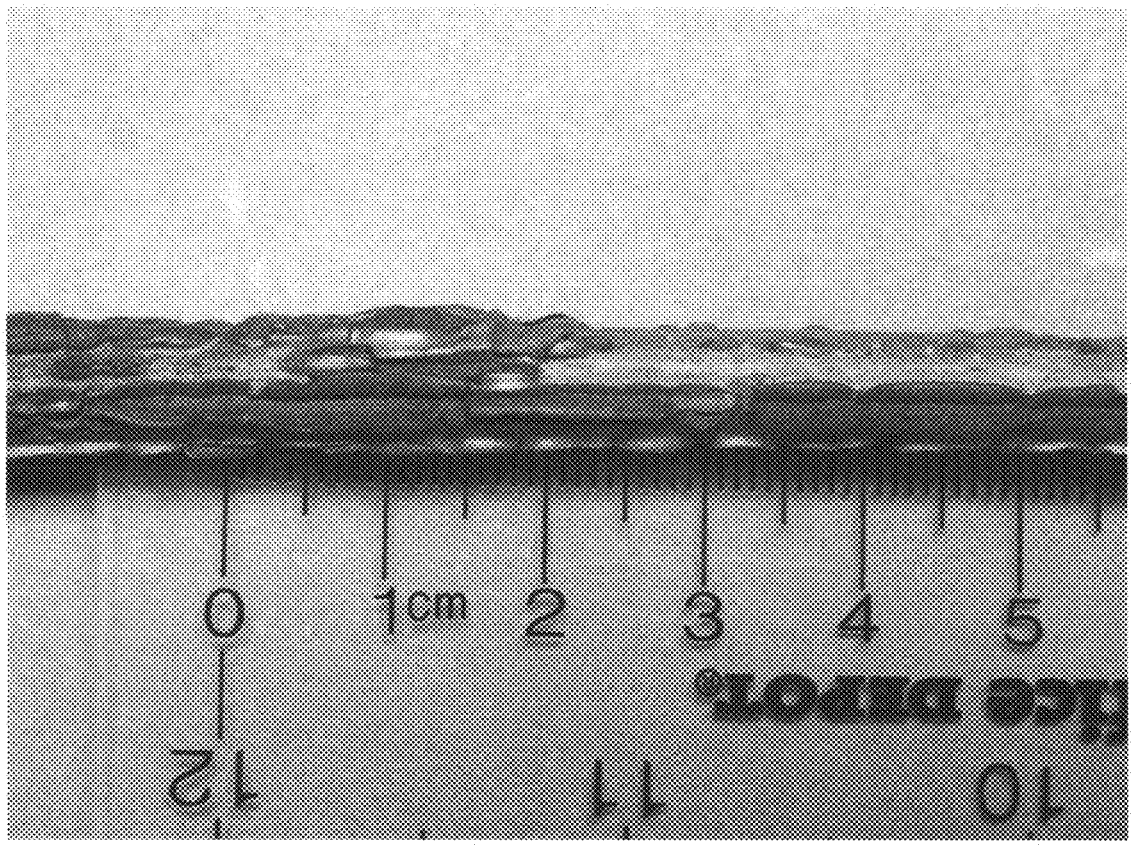
FIG. 9: Shows a close up of a portion of a first year branch from a tree of my new variety during the winter season, illustrating the development of corky ridges on the branch surface.

The following detailed description of the 'JFS-KW3' variety, with color terminology in accordance with The Royal Horticultural Society (R.H.S.) Colour Chart, 1986 Edition, published by The Royal Horticultural Society in London, and is based on observations of the original tree and one, two, and three year old progeny. The observed progeny were trees which were growing in Boring, Oreg.

Scientific name: *Quercus macrocarpa* 'JFS-KW3'.

Parentage:

*Seed parent*.—Unnamed, unpatented tree of the species *Quercus macrocarpa*.

*Pollen parent*.—Unnamed, unpatented tree of the species *Quercus macrocarpa*.

Tree:

*Overall shape*.—Tall, straight, upright, narrowly pyramidal to narrowly oval.

*Height*.—Original tree, 9.3 meters at 13 years of age.

*Width*.—Original tree, 2.1 meters at 13 years of age.

*Caliper*.—Original tree, 16.3 cm at 10 cm from ground; 13.0 cm at 1 meter, at 13 years of age.

*Trunk*.—Original tree, sturdy, straight, deeply furrowed, with a straight leader.

*Trunk bark texture*.—Original tree, deeply furrowed with rough corky bark ridges.

*Trunk bark color*.—Immature bark color: Grey-brown 199A, with corky ridges that are Greyed-orange 165B to Brown 200C. Mature bark color: Greyed-brown 197B to Grey 201A. Lenticels: None visible on trunk.

*Primary branches*.—Short, sturdy, with wide branch angles.

*Branch angle*.—Varies from 40 degrees to 90 degrees, but typically 60 to 90 degrees.

*Branch lenticels*.—Small, round, 0.5 mm by 0.5 mm, Greyed-orange 165D to Orange-white 159A. As branches grow, the lenticels become engulfed in the developing corky bark.

*Branch bark*.—Smooth at first, becoming irregularly roughened with corky ridges during the first season. Branch bark color: Grey-Green 197A to Grey-Brown 199B. Corky ridges are 1 mm to 4 mm high during the first season. Branch corkiness is patchy during the first two seasons, then branches generally become completely corky by the end of the third season.

*Dormant buds*.—Generally triangular in shape with a bluntly acute tip, 2 mm to 5 mm long by 2 mm to 3.5 mm wide. Overlapping scales, mostly two ranked, cover the buds. Short pubescence covers scales. Dormant bud color: Grey-Brown 199C to 199D.

*Internodes*.—1.9 cm to 4.0 cm.

*Hardiness*.—Has tolerated temperatures to 10 degrees F. without damage in Boring, Oreg. It has not been tested at lower temperatures, but it is believed to have Zone 3 cold hardiness similar to the species.

*Disease resistance*.—Highly resistant to powdery mildew (*Erysiphe alphitoides*) and anthracnose (*Apiognomonia quercina*).

Leaves:

*Except as otherwise noted, observations are from twenty typical vigorous growth leaves.*

*Arrangement*.—Alternate.

*Texture*.—Thick, smooth.

*Sheen*.—Very glossy upper surface, dull under surface.

*Length*.—13 cm to 21 cm.

*Width*.—7 cm to 12 cm.

*Petioles*.—1 cm to 1.5 cm long×2 mm wide (diameter). The color of the petioles vary through the growing season and with the degree of exposure to sunlight. In Spring, the petioles are Green 140C; in early Summer, they change to Yellow-Green 145A; in late Summer, portions of the petioles exposed to sunlight change to Greyed-Red 181C, and in the Fall, the petiole color changes to Yellow-Orange 22A to Greyed-Orange 163B.

*Overall shape and orientation*.—Obovate, with rounded lobes.

*Leaf orientation*.—Leaf angled upward at petiole attachment.

*Margin*.—Lobed with 4 to 7 variably shaped lobes. The basal lobes are generally cut more than halfway to the mid-rib and the upper lobes are generally shallowly cut. The lobes become reduced to an irregularly undulate margin at the tip.

*Tip*.—Obtuse to rounded.

*Base*.—Cuneate.

*Stipules*.—None.

*Spring leaf color, first emerging leaves*.—Top surface Green 140B. Lower surface Green 140D.

*Summer leaf color*.—Upper leaf surface: Green 139A. Lower leaf surface: Yellow-Green 148C to Yellow-Green 149D. Vein: Yellow-Green 145C on underside, Yellow-Green 153C on top.

*Fall leaf color*.—Top surface Yellow-Orange 19A to Yellow-Orange 21B.

*Pubescence*.—White 157D in color; Underside — tomentulose with dense short tomentum. Top — sparse, scattered stellate hairs.

*Persistence*.—Tree is deciduous.

Flowers:

*Overall*.—Monoecious, with male flowers held in pendulous catkins and female flowers held generally in pairs on short stalks in the axils of leaves.

*Catkin and flowers* (*observed in original tree*).—Male — Long pendulous, cylindrical, many flowered catkins averaging 3 cm to 8 cm long by 3 mm to 5 cm wide. Yellow-green 151A to 151C. Stalk slightly pubescent, pubescence White 157D in color. Individual flowers consist of a highly reduced calyx with generally five protruding stamens. Anthers Yellow 13A. Female — Generally held in pairs or occasionally threes on a 2 mm to 5 mm long stalk in leaf axils. Flowers are typically 3 mm by 3 mm overall, Yellow-green 145A. The calyx is reduced to bracts surrounding a globose ovary with a three lobed pistil. Stigma color is Yellow-green 154B.

*Fragrance*.—None.

*Flowering date*.—In Boring, Oreg., original tree had a peak bloom May 20, during the 2009 growing season.

Fruit: Observations are from a sampling of typical fruit from the original tree as the progeny are too young to have produced any acorns.

*Type*.—Acorn, consisting of a nut and a cap that surrounds the top one-third to one-half of the nut.

*Size*.—Overall, acorn averages 18 mm long by 15 mm in diameter at widest location. Nut is 17 mm long×13 mm in diameter at the widest location. Cap is 15 mm in diameter at the widest location×9 mm high. Stalk varies from 2 mm to 12 mm long×1 mm to 2 mm in diameter.

*Shape*.—Ovoid, smooth nut with rounded, scaled cap. Cap margin with long, wavy scales giving a fringed appearance.

*Color*.—Nut — Greyed-Orange 165B to Greyed-Orange 165C. Cap — Greyed-Green 197A to Greyed-Green 197C.

*Seeds*.—Fleshy to firm, ovoid, 14 mm×9 mm, Greyed-Orange 165A when mature. Surface is finely rugose.

*Fruit production*.—Moderate.

*Usage*.—Food source for wild life.

Comparison to the species: My new variety is taller and more narrow in form than the species. The 13 year old original tree is best described as narrowly pyramidal to narrowly oval in shape, while typical trees of the species are broadly oval at the same age. Measurement of propagated one and two year old trees of my new variety and seedlings of the species confirm this form difference. This, and other differences are detailed in Table 1 below.

TABLE 1

| Feature: | 'JFS-KW3' | Seedling |
|---|---|---|
| Height, 1 year tree | 1.75 meter | 1.09 meter |
| Height, 2 year tree | 2.59 meter | 2.44 meter |
| Longest branch, 2 year | 38 cm | 66 cm |
| Ratio of Height to Longest branch | 6.8 to 1 | 3.7 to 1 |
| Leaf upper surface | Glossy | Dull |
| Leaf color, upper surface | Green 139A | Yellow-green 144A to Green 139A |
| Leaf orientation | Upward along branch | Outward from branch |
| Petiole angle from branch | 20° to 50° | 80° to 110° |
| Acorns | Observed in original tree only, small, 18 mm long by 15 mm in diameter at the widest location | Large, typically 20 mm to 40 mm long by 18 to 35 mm in diameter at the widest location |

I claim:

1. A new and distinct variety of bur oak tree, substantially as herein shown and described.

* * * * *